(12) United States Patent
Katsuda et al.

(10) Patent No.: US 8,080,564 B2
(45) Date of Patent: Dec. 20, 2011

(54) HEMODYNAMICS IMPROVING AGENT

(75) Inventors: Shin-ichiro Katsuda, Fukushima (JP);
Akihiro Hazama, Fukushima (JP);
Naoto Koyama, Kawasaki (JP);
Katsuya Suzuki, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 105 days.

(21) Appl. No.: 12/048,510

(22) Filed: Mar. 14, 2008

(65) Prior Publication Data

US 2008/0171781 A1 Jul. 17, 2008

Related U.S. Application Data

(63) Continuation of application No. PCT/JP2006/318668, filed on Sep. 14, 2006.

(30) Foreign Application Priority Data

Sep. 14, 2005 (JP) ................................ 2005-267286

(51) Int. Cl.
*A61K 31/445* (2006.01)
*A61K 36/00* (2006.01)

(52) U.S. Cl. ........................................ 514/315; 424/776

(58) Field of Classification Search .................. 514/315; 424/776
See application file for complete search history.

(56) References Cited

U.S. PATENT DOCUMENTS

| 2005/0136137 A1 | 6/2005 | Koyama et al. |
| 2006/0257540 A1 | 11/2006 | Koyama et al. |

FOREIGN PATENT DOCUMENTS

| CN | 1500499 A | 6/2004 |
| EP | 1 132 389 A1 | 9/2001 |
| EP | 1 495 765 A1 | 1/2005 |
| JP | 10-287576 | 10/1998 |
| RU | 2 201 262 C2 | 3/2003 |
| WO | WO 2005/034975 A1 | 4/2005 |

OTHER PUBLICATIONS

Yoshihiro Hotta, et al., "Protective effects of antioxidative serotonin derivatives isolated from safflower against postischemic myocardial dysfunction", Molecular and Cellular Biochemistry, vol. 238, No. 1 & 2, 2002, pp. 151-162.

Kameyama H, et al., Hypertens Res. vol. 28, No. 5 (2005) pp. 439-445.

Extended European Search Report dated Jan. 12, 2011 in European Patent Application No. 06798165.4 filed Sep. 14, 2006.

Moon Kwang-Deog, et al., "Safflower seed extract lowers plasma and hepatic lipids in rats fed high-cholesterol diet", Nutrition Research 21 (2001) 895-904.

Dermot Kenny, et al., "Effect of Omega-3 Fatty Acids on the Vascular Response to Angiotensin in Normotensive Men", The American Journal of Cardiology, vol. 70, Nov. 15, 1995, pp. 1347-1352.

Hirofumi Tomiyama, et al., "Non-Invasive Vascular Function Tests: Their Pathophysiological Background and Clinical Application", Circulation Journal, vol. 74, Jan. 2010, pp. 24-33.

Wendy L. Hall, "Dietary saturated and unsaturated fats as determinants of blood pressure and vascular function", Nutrition Research Reviews (2009), 22, pp. 18-38.

*Primary Examiner* — Kevin E Weddington
(74) *Attorney, Agent, or Firm* — Oblon, Spivak, McClleland, Maier & Neustadt, L.L.P.

(57) ABSTRACT

Agents which contains a serotonin derivative as an active ingredient are effective for improving hemodynamics and for preventing or improving deterioration of hemodynamics associated with aging and progression of cardiovascular diseases.

19 Claims, 6 Drawing Sheets

HEMODYNAMICS IMPROVING AGENT

CROSS REFERENCES TO RELATED APPLICATIONS

This application is a continuation of International Patent Application No. PCT/JP2006/318668, filed on Sep. 14, 2006, and claims priority to Japanese Patent Application No. 2005-267286, filed on Sep. 14, 2005, both of which are incorporated herein by reference in their entireties.

BACKGROUND OF THE INVENTION

1. Field of the Invention

The present invention relates to an agent for improving hemodynamics. The present invention also relates to methods for improving hemodynamics.

2. Discussion of the Background

With the westernization of lifestyle in recent years, diseases such as angina pectoris, myocardial infarction, cerebral infarction and the like, along with cancer, have become the primary cause of deaths of Japanese people. In addition, complications developed with the progression of diabetes, such as nephropathy, retinopathy and the like, increase kidney dialysis and bedridden patients, forming a biggest cause straining the medical expenses. All of these are diseases in the blood vascular system, which are extremely difficult to cure after onset and significantly degrade the QOL (quality of life) of patients. Therefore, an arrangement to always keep damage to blood vessels and the level of aging within appropriate ranges is extremely important also from social aspects.

As risk factors that damage blood vessels and accelerate aging, hyperlipidemia, hyperglycemia, hypertension, obesity and the like are conventionally known. High blood lipid, blood glucose, blood pressure and the like are known to reduce the extensibility of blood vascular walls and change reactivity with various vascular tonus regulatory factors such as nitric oxide (NO) and angiotensin II. Therefore, control of these risk factors to appropriate levels is important, and drugs, food and the like for this object have been continuously developed. Even when the levels of these risk factors are the same, the damage to and aging of blood vessels are interindividually different and cannot be consistent. Therefore, direct measurement of the level of aging of blood vessels becomes important. Recently, it is becoming possible to noninvasively and quantitatively evaluate the aging level of blood vessels by measuring and analyzing changes in the arterial blood pressure due to heartbeat, i.e., pulse wave. In as much as pulse wave velocity (PWV) showing the velocity of the pulse wave along an artery, Augmentation Index (AIx) reflecting the total peripheral vascular resistance, particular wave form component of second derivative of photoplethysmogram, which is the laplacian of the digital plethysmogram finger plethysmogram, as well as a numerical index consisting thereof and the like show certain changes with aging (Schiffrin, Am. J. Hypertens., 17: 395, 2004, and Takazawa, et. al., Hypertension, 32:365, 1998), the concept of "vascular age" based on the standard value for each age is prevailing.

In recent clinical tests, moreover, the number of reports showing the usefulness of PWV, AIx and the like as risk prediction factors of cardiovascular diseases is increasing (Boutuyrie, et. al., Hypertension, 39:10, 2002, and London, et. al., Hypertension, 38:434, 2001). While these indices are considered to mainly reflect extensibility, wall thickness and vascular resistance of blood vascular walls, it is clear that they are not defined only by blood pressure or mere structural stiffness, in view of the reports documenting examples showing that PWV changes differently even when the level of hypotensive effect is the same (Asmar, et. al., J. Hypertens., 19:813, 2001), and that these indices are improved by a light exercise therapy (Sugawara et al., abstract of the third meeting of Clinical Arterial Wave Society, 39, 2003) or a short-term intervention of a certain drug (Matsuo et al., abstract of the second meeting of Clinical Arterial Wave Society, 33, 2002, and Watanabe, et. al., American College of Cardiology 51st Annual Scientific Session, 2002). Involvement of factors such as sympathetic nerve activity, vascular endothelial function, adiponectin and the like is also suggested (McVeigh, et. al., Arterioscler. Thromb. Vasc. Biol., 14: 1425, 1994, Agata, et. al., Circul. J., 68: 1194, 2004 and Akimoto et al., 'Pulse wave velocity', 104, MEDICA1 VIEW, 2002), and therefore, these indices are taken as indices of total risk for vascular walls including temporary functional vascular tone rather than mere indices of atherosclerosis.

Therefore, a component capable of directly improving a pulse wave-related index such as PWV, AIx and the like and maintaining the "vascular age" within an appropriate range is highly likely more useful for the prophylaxis or treatment of cardiovascular diseases than a component that indirectly decreases a blood vessel risk through improvement of classic indices such as blood cholesterol, blood pressure and the like. The number of reports relating to a PWV improving effect by a part of pharmaceutical products (statin, angiotensin II receptor blocker, EPA preparation and the like) is increasing in recent years (Agata, et al., Circul. J., 68:1194, 2004, Asmar, 'Pulse wave velocity and therapy', 142, Elsevier, 1999 and Sato, et al., J. Cardiovasc. Pharmacol., 22: 1, 1993). The report on a lower incidence of cardiovascular event in a group showing a good PWV improvement rate, though with a similar level of hypotensive action (Yamashina, Toyama, 'Pulse wave velocity', 120, MEDICA1 VIEW, 2002) is one such example. However, long-term consecutive use of these pharmaceutical products may cause adverse effects, and there have been found only a few food components considered to be safer and known to improve PWV, AIx, second derivative of photoplethysmogram waveform (Teede, et al., Arterioscler. Thromb. Vasc. Biol., 23: 1066, 2003 and Nestel, et al., Arterioscler. Thromb. Vasc. Biol., 17: 1163, 1997).

The composition for improvement of hemodynamics of the present invention, as mentioned below, suppresses an increase of the pulse wave velocity (PWV) and Augmentation Index (AIx) in rabbit, as well as decreases the blood pressure (systolic blood pressure, mean blood pressure) and pulse pressure. While these hemodynamic indices are known to increase as atherosclerosis progresses, it is known that they are also degraded by, in addition to structural stiffening of blood vessels, an increase in the total vascular resistance due to promoted functional vascular tone.

SUMMARY OF THE INVENTION

Accordingly, it is one object of the present invention to provide novel agents for improving hemodynamics.

It is another object of the present invention to provide novel agents for improving hemodynamis, which prevent or improve aggravation of hemodynamics due to aging or progression of cardiovascular diseases.

It is another object of the present invention to provide novel methods for improving hemodynamics.

It is another object of the present invention to provide novel methods for improving or preventing aggravation of hemodynamics due to aging or progression of cardiovascular diseases.

These and other objects, which will become apparent during the following detailed description, have been achieved by the inventors' discovery that serotonin derivatives have an effect of preventing or improving aggravation of hemodynamics, which resulted in the completion of the present invention.

Accordingly, the present invention provides the following:

(1) An agent for improving hemodynamics, comprising at least one serotonin derivative as an active ingredient.

(2) The agent of (1), wherein said hemodynamics improvement is selected from the group consisting of improvement of vascular age, improvement of blood pressure and improvement of pulse pressure.

(3) The agent of (2), wherein the improvement of vascular age is selected from the group consisting of improvement of a pulse wave velocity (PWV), improvement of Augmentation Index (AIx), improvement of second derivative of photoplethysmogram waveform and improvement of a second derivative of photoplethysmogram aging index.

(4) The agent of any of (1) to (3), wherein the serotonin derivative is a compound represented by formula (I)

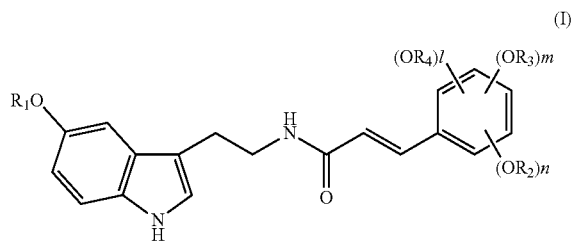

wherein $R_1$, $R_2$, $R_3$, and $R_4$ are each independently a hydrogen atom, or an alkyl group having 1 to 3 carbon atoms, and n, m, and l are each 0 or 1, or a glycoside thereof.

(5) The agent of (4), wherein said serotonin derivative is at least one kind selected from the group consisting of serotoninamide of hydroxycinnamic acid and a glycoside thereof.

(6) The agent of (5), wherein the hydroxycinnamic acid is at least one kind selected from the group consisting of p-coumaric acid, ferulic acid and caffeic acid.

(7) The agent of any of (1) to (6), wherein said serotonin derivative is contained in an extract from a plant tissue.

(8) The agent of (7), wherein said plant tissue is a safflower seed.

(9) The agent of any of (1) to (8), wherein said serotonin derivative is contained in an organic solvent extract from a safflower seed before or after oil extraction.

(10) A method of improving hemodynamics in a subject, comprising administering the agent of any of (1) to (9) to a subject in need thereof.

(11) Use of a serotonin derivative for the production of an agent for improving hemodynamics.

(12) Use of (11), wherein the serotonin derivative is a compound represented by the following formula (I)

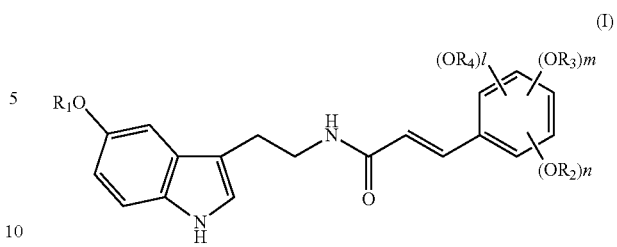

wherein $R_1$, $R_2$, $R_3$, and $R_4$ are each independently a hydrogen atom, or an alkyl group having 1 to 3 carbon atoms, and n, m, and l are each 0 or 1, or a glycoside thereof.

(13) Use of (12), wherein said serotonin derivative is at least one kind selected from the group consisting of serotoninamide of hydroxycinnamic acid and a glycoside thereof.

(14) Use of (13), wherein the hydroxycinnamic acid is at least one kind selected from the group consisting of p-coumaric acid, ferulic acid and caffeic acid.

(15) The use of any of (11) to (14), wherein said serotonin derivative is contained in an extract from a plant tissue.

(16) The use of (15), wherein said plant tissue is a safflower seed.

(17) The use of any of (11) to (16), wherein said serotonin derivative is contained in an organic solvent extract from a safflower seed before or after oil extraction.

(18) A pharmaceutical composition comprising the agent of any of (1) to (9).

(19) A food comprising the agent of any of (1) to (9).

(20) A commercial package comprising the agent of any of (1) to (9) and a written matter stating that the agent can or should be used for improving hemodynamics.

(21) A food for improving hemodynamics comprising a serotonin derivative.

(22) The food of (21), wherein said improvement of hemodynamics is selected from the group consisting of improvement of vascular age, improvement of blood pressure and improvement of pulse pressure.

(23) The food of (22), wherein the improvement of vascular age is selected from the group consisting of improvement of a pulse wave velocity (PWV), improvement of Augmentation Index (AIx), improvement of a second derivative of photoplethysmogram waveform and improvement of a second derivative of photoplethysmogram aging index.

(24) The food of any of (21) to (23), wherein the serotonin derivative is a compound represented by the following formula (I)

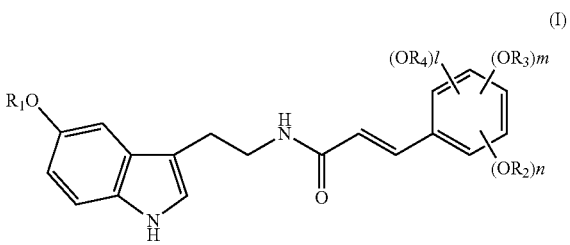

wherein $R_1$, $R_2$, $R_3$, and $R_4$ are each independently a hydrogen atom, or an alkyl group having 1 to 3 carbon atoms, and n, m, and l are each 0 or 1, or a glycoside thereof.

(25) The food of (24), wherein said serotonin derivative is at least one kind selected from the group consisting of serotoninamide of hydroxycinnamic acid and a glycoside thereof.

(26) The food of (25), wherein the hydroxycinnamic acid is at least one kind selected from the group consisting of p-coumaric acid, ferulic acid and caffeic acid.

(27) The food of any of (21) to (26), wherein said serotonin derivative is contained in an extract from a plant tissue.

(28) The food of (27), wherein said plant tissue is a safflower seed.

(29) The food of any of (21) to (28), wherein said serotonin derivative is contained in an organic solvent extract from a safflower seed before or after oil extraction.

(30) A food for improving hemodynamics, comprising 5-180 mg of a serotonin derivative per unit package.

(31) The food of any of (21) to (30), which is a food with health claims.

(32) The food of (31), which is a food for specified health uses.

(33) The food of any one of (21) to (32), having an indication that the food is used for improving hemodynamics.

(34) A commercial package comprising the food of any one of (21) to (32) and a written matter describing an explanation relating to the use for improving hemodynamics.

The composition for improvement of hemodynamics of the present invention suppresses an increase of the pulse wave velocity (PWV) and Augmentation Index (AIx) in rabbit, as well as decreases the blood pressure (systolic blood pressure, mean blood pressure) and pulse pressure. While these hemodynamic indices are known to increase as atherosclerosis progresses, it is known that they are also degraded by, in addition to structural stiffening of blood vessels, an increase in the total vascular resistance due to promoted functional vascular tone.

It has already been reported that an extract from defatted safflower seed prevents formation of an atherosclerosis lesion (see, WO03/086437). However, improvement of these hemodynamic indices by the present invention is irrelevant to the formation of an atherosclerosis lesion. It mainly improves the functional tension of blood vessels and decreases the total vascular resistance, whereby hemodynamics is improved.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 1:
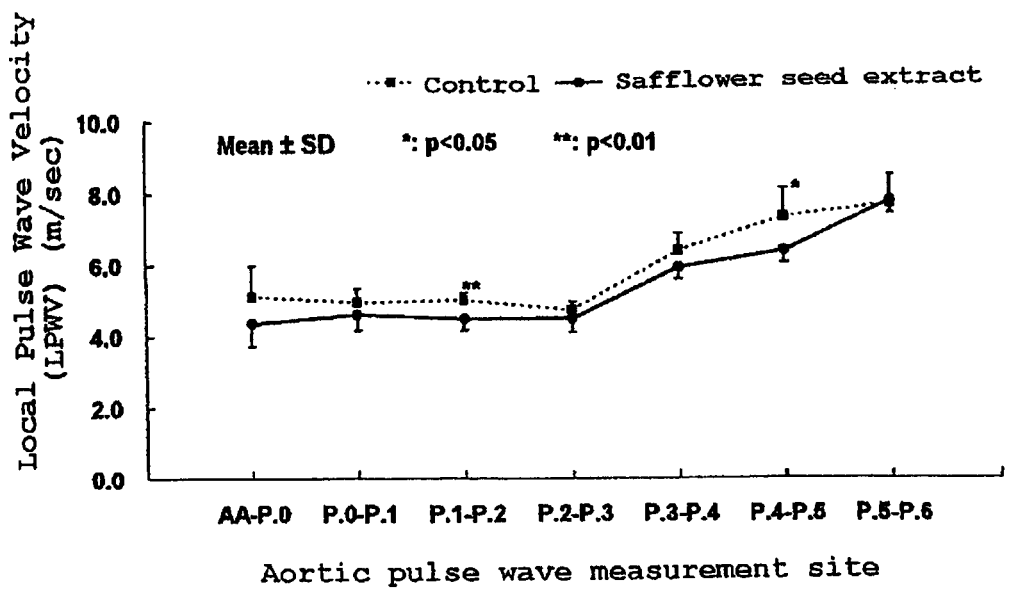
FIG. 1 shows local pulse wave velocity in 4 week cholesterol loaded KHC rabbit aorta in Example 3. The horizontal axis shows an aortic region where the pressure pulse wave was measured (AA-P.0=ascending aorta-distal end of aortic arch, P.0-P.1=distal end of aortic arch-thoracic aortic proximal portion, P.1-P.2=thoracic aortic proximal portion-thoracic aortic midportion, P.2-P.3=thoracic aortic midportion-thoracic aortic distal portion, P.3-P.4=thoracic aortic distal portion-abdominal aortic proximal portion, P.4-P.5=abdominal aortic proximal portion-abdominal aortic midportion, P.5-P.6=abdominal aortic midportion-abdominal aortic distal portion).

The present invention relates to an agent for improving hemodynamics, which comprises at least one serotonin derivative as an active ingredient.

In the present specification, the improvement of hemodynamics refers to an improvement of vascular function, more specifically, at least one selected from an improvement of vascular age, an improvement of blood pressure and an improvement of pulse pressure, which can be known from pulse wave-related indices such as improvement of pulse wave velocity (PWV), Augmentation Index (AIx), second derivative of photoplethysmogram waveform, second derivative of photoplethysmogram aging index and the like.

The pulse wave velocity (PWV) is determined by attaching pressure sensors to the carotid artery, inguinal artery, brachial, ankle and the like, and measuring the distance between the sensors and time-lag between pulse waves. Depending on the difference in the pulse wave measurement parts, it includes baPWV (brachial-ankle), cfPWV (carotid artery-femoral artery) and the like, as well as blood pressure-adjusted CAVI (Cardio Ankle Vascular Index) and the like. These are used as indices of vascular age, extensibility of blood vessel, extent of sclerosis and the like. Here, the improvement thereof means reduction of or suppression of an increase in the PWV value.

The Augmentation Index (AIx) is obtained by, for example, dividing a secondary pressure increase (augmentation pressure) observed during the midsystole of the arterial blood pressure waveform measured according to a tonometry method or oscillometry method by the pulse pressure (difference between the systolic blood pressure and the diastolic blood pressure). Since it indicates the ratio of the reflection wave component, AIx is used as an index of the total vascular resistance, afterload on the heart and the like. Here, the improvement thereof means a reduction of or suppression of an increase in the AIx value.

The second derivative of photoplethysmogram is obtained by twice differentiating plethysmography (photoplethysmogram) measured by irradiating a fingertip and receiving the permeated light or reflected light thereof. It has been reported that the 5 components (waves a-e) constituting its waveform increase or decrease with aging. In particular, the ratio of wave b to wave a (b/a) is used as an index of the extensibility of blood vessel, and the ratio of wave d to wave a (d/a) is used as an index of the structural extent of sclerosis blood vessel, and the functional tone mainly represented by an increase in the internal blood vessel pressure. The second derivative of photoplethysmogram aging index, i.e., (b-c-d-e)/a, and the "vascular aging deviation value" (U-Medica Inc.) obtained by statistically analyzing pulse waves are used as indices for estimating the aging level of the blood vessel and vascular age. Here, the improvement thereof means a decrease in b/a, an increase in c/a, d/a or e/a, or any of these.

An improvement of vascular age means that an estimated vascular age calculated based on the second derivative of photoplethysmogram aging index or the vascular aging deviation value becomes closer to the calendar age, or the PWV value becomes closer to the age specific standard value.

The pulse pressure means a difference between the systolic blood pressure and the diastolic blood pressure, and the improvement thereof means prevention of a decrease in the systolic blood pressure or a decrease in the diastolic blood pressure.

The improvement of blood pressure means reduction of blood pressure in hypertension, particularly reduction of average blood pressure and reduction of systolic blood pressure.

In the present specification, the "improvement" of the "improvement of hemodynamics" is a concept including prevention of aggravation and maintenance of the current level, in addition to the aforementioned various improvements.

As the serotonin derivative to be used in the present invention, serotonin amide of hydroxycinnamic acid is a preferably exemplified. For example, a compound represented by the following formula (I) is included.

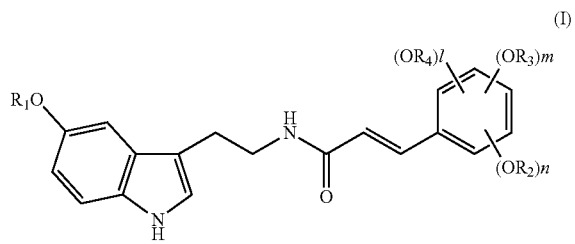

wherein $R_1$, $R_2$, $R_3$, and $R_4$ are each independently a hydrogen atom, or an alkyl group having 1 to 3 carbon atoms, and n, m, and l are each 0 or 1. In the present specification, the alkyl group has 1 to 3 carbon atoms. Examples thereof include methyl, ethyl, n-propyl and i-propyl.

Preferable examples of hydroxycinnamic acid include p-coumaric acid, ferulic acid and caffeic acid. Examples of serotonin amide thereof include p-coumaroyl serotonin (or p-coumarilic serotonin), feruloyl serotonin (or ferulyl serotonin) and caffeoyl serotonin.

Examples of the aforementioned glycoside of serotonin derivative include, but are not limited to, O-β-D-glucopyranoside wherein β-glucoside linkage is formed between glucose for $R_1$ and compound (I), and the like.

As the serotonin derivative, the above-mentioned compounds can be used alone, or in a combination thereof.

A serotonin derivative can be prepared by chemical synthesis or extraction from a naturally occurring substance.

The compound is known per se, and can be synthesized by a method known per se.

When a serotonin derivative is extracted from a naturally occurring substance, various plant tissues can be used as starting materials. For example, a seed of Asteraceae plants such as safflower and knapweed, kernel and plant tuber of Japanese barnyard millet, elephant foot and the like, and the like can be mentioned, with preference given to safflower seed and defatted grounds thereof. In the present invention, the plant seed may be the whole constituting the plant seed, a part thereof, for example, seed coat, endosperm, germ and the like taken out therefrom, or a mixture thereof. As an extraction method from these, for example, the following methods can be mentioned.

Plant tissues are generally subjected to extraction as defatted material (meal). Defatted material can be obtained by a method known per se, such as defatting plant tissues (e.g., plant seeds). For example, it can be obtained by press-extracting seeds, or extracting crushed seeds with n-hexane and the like, then separating a solid content from the extraction system, and drying the solid content. A rough level of defatting is generally not less than 60 wt %, preferably not less than 80 wt %, relative to the total fat content before defatting.

An example of the extraction method includes washing defatted plant seeds with water, and extracting them with an organic solvent.

Water is not particularly limited. For example, all of distilled water, tap water, industrial water, a mixture of these and the like can be used. Water may contain other substances, such as inorganic salts (e.g., sodium chloride, potassium chloride, calcium chloride etc.), acid (e.g., hydrogen chloride, acetic acid, carbonic acid, hydrogen peroxide, phosphoric acid etc.), alkali (e.g., sodium hydroxide, potassium hydroxide, sodium hydrogencarbonate etc.) and the like, as long as the effect of the present invention can be afforded. During washing, the pH is generally 2 to 9, preferably 5 to 7.

The total amount of water to be used is generally 2- to 100-fold amount (water volume/defatted plant seed weight, hereinafter the same), preferably 10- to 40-fold amount, relative to the defatted plant seed (starting material).

For washing, a defatted plant seed (starting material) is brought into contact with water by a method known per se. For example, a method in which a defatted plant seed is suspended in water, filtered, and the solid after washing treatment is recovered, and the like can be used. For washing, water in the above-mentioned amount may be brought into contact with defatted plant seed at once or in plural times, or continuously. The temperature during contact is generally 5 to 45° C., preferably 25 to 35° C. The contact time is generally 10 to 240 min, preferably 15 to 60 min.

The defatted plant seed and the like obtained as mentioned above can be washed and then extracted with an organic solvent to give an extract of the plant seed and the like.

Examples of the organic solvent include, but are not limited to, lower alcohol, acetone, acetonitrile and a mixed solvent thereof and the like. The organic solvent may contain water or may be anhydride. The concentration of the organic solvent is generally 20 to 95 wt %, preferably 50 to 90 wt %. In consideration of concentration, drying and food production of an extract after extraction, the organic solvent is preferably a lower alcohol. Examples of the lower alcohol include, but are not limited to, alcohols having 1 to 4 carbon atoms, specifically methanol, ethanol, n-propanol, isopropanol, n-butanol, and the like. From the aspects of food production, the lower alcohol is preferably ethanol. The ethanol is preferably water-containing ethanol or anhydrous ethanol having an ethanol content of not less than 50 wt %.

The amount of the organic solvent to be used is generally 2- to 40-fold amount (organic solvent volume/defatted plant seed weight, hereinafter the same), preferably 2- to 10-fold amount, relative to the defatted plant seed (starting material). The extraction temperature is generally 20 to 75° C., preferably 50 to 70° C. The extraction time is generally 10 to 240 min, preferably 60 to 120 min.

During extraction of a plant tissue, washing with water can be omitted.

Moreover, undefatted plant tissues such as undefatted plant seeds and the like may also be pulverized or compressed with, for example, a roller or the like, and extracted with the aforementioned organic solvent or the like to give an extract.

After extraction, the solid content is separated from the suspension by filtration or the like, and the obtained extract may be used as it is or, where necessary, used after concentration and drying, as the plant seed extract of the present invention. For concentration and drying, the extract may be concentrated or dried as it is, or may be concentrated or dried after addition of an excipient (e.g., lactose, sucrose, starch, cyclodextrin, etc.). While the extract obtained by extraction with the above-mentioned solvent may be used in the present invention at that purity, it may be further purified according to a method known per se.

One example for further increasing the purity is described, but the method is not limited thereto. The organic solvent of the aforementioned solvent extract is evaporated under reduced pressure; water is added thereto; the extract is suspended in the water; the aqueous phase is washed with a nonpolar solvent, for example, n-hexane, n-heptane, n-octane or the like, preferably n-hexane; and the aqueous layer after washing is extracted with a solvent that can extract the desired composition by separating the aqueous layer into two layers, such as acetate, n-butanol or the like, preferably ethyl acetate, methyl acetate, propyl acetate, etc. Then, the extract is washed with saturated brine or the like to obtain an organic layer. When extracted with acetate ester, the organic layer is dehydrated with, for example, anhydrous magnesium sulfate or the like and then concentrated under reduced pressure to give a solid (composition). Purification may be ceased at any stage mentioned above, any step may be omitted or modified, and additional purification may be performed. Including changing the kind of the above-mentioned solvent, a multi-step extraction method, a countercurrent distribution method and the like may also be used.

The serotonin derivative in the present invention can be used as an active ingredient of a pharmaceutical agent or food for improving hemodynamics in animals including human (mammals such as human, bovine, swine, dog, cat and the like, birds such as chicken and the like, etc.).

Moreover, the serotonin derivative in the present invention can be used as an agent for improving hemodynamics contained in a food (food composition) or a pharmaceutical preparation (pharmaceutical composition), by formulating a preparation in the form of tablet, pill, granules, fine granules, powder, pellet, capsule, solution, emulsion, suspension, syrup, troche and the like together with an excipient (e.g., lactose, sucrose, starch, cyclodextrin etc.) and, when demanded, flavor, corrigent, dye, seasoning, stabilizer, preservative and the like.

While the "food" in the present invention means food in general, it also includes general foods including what is called a health food, as well as food with health claims defined in the food with health claims system of the Ministry of Health, Labour and Welfare of Japan, such as food for specified health uses and food with nutrient function claims and the like, and the like. Moreover, supplement, feed, food additive and the like are also encompassed in the food of the present invention.

When the food of the present invention is ingested with an expectation of improving hemodynamics, it can be drunk or eaten in various forms. It is preferable to provide unit packaging of an amount to be ingested at one time, thereby teaching a general amount to be ingested for one time. The amount of the serotonin derivative for one unit packaging is recommended to be 5 to 180 mg, preferably 10 to 150 mg, more preferably 20 to 120 mg. The amount of the serotonin derivative in this case is detected by HPLC (column: SHISEIDO Capcell Pak ODS UG-120, 3 μm (φ4.6×250 mm), developing solvent: 25 min linear gradient from 0.1% trifluoroacetic acid-20% aqueous acetonitrile solution to 0.1% trifluoroacetic acid-40% aqueous acetonitrile solution, developing solvent flow rate: 0.8 m/min, detector: UV (290 nm)), and is the sum of serotonin derivatives (p-coumaroyl serotonin (CS) and feruloyl serotonin (FS)) represented by the following formula.

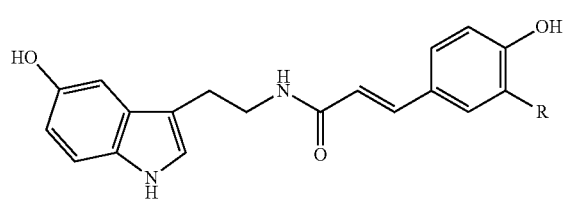

R = H: p-coumaroyl serotonin
R = OCH$_3$: feruloyl serotonin

The agent for improving hemodynamics of the present invention is used as a pharmaceutical agent or food.

When the food of the present invention is ingested for the purpose of improving hemodynamics, it can be provided in a form carrying an indication that the food is used for improving hemodynamics.

Moreover, the food of the present invention can also be provided as a commercial package containing a written matter with an explanation regarding use for improving hemodynamics.

As the food, for example, a serotonin derivative may be contained in a general food (including what is called a health food) such as dressing, mayonnaise and the like. Moreover, a serotonin derivative can be used as a food with health claims such as food for specified health uses, food with nutrient function claims and the like, supplement, pharmaceutical preparation (pharmaceutical composition) (mainly oral) by formulating a tablet, pill, granules, fine granules, powder, pellet, capsule, solution, emulsion, suspension, syrup, troche and the like together with an excipient (e.g., lactose, sucrose, starch etc.) and, when demanded, flavor, dye and the like. In addition, a serotonin derivative can also be applied to feed. For fowl, domestic animal and the like, it can be ingested or administered by addition to a general feed.

Particularly, when used as a pharmaceutical agent, the derivative can be formulated into a preparation together with a carrier (including additives) acceptable as a pharmaceutical agent. Examples of the pharmaceutically acceptable carrier include, but are not limited to, excipient (e.g., lactose, sucrose, dextrin, hydroxypropylcellulose, polyvinylpyrrolidone etc.), disintegrant (e.g., starch, carboxymethylcellulose etc.), lubricant (e.g., magnesium stearate etc.), surfactant (e.g., sodium lauryl sulfate etc.), solvent (e.g., water, brine, soybean oil etc.), preservative (e.g., p-hydroxybenzoate etc.) and the like.

The method of ingestion or administration of the agent for improving hemodynamics of the present invention varies depending on the age, body weight and health condition of the administration subject. When, for example, maintenance or enhancement of health or prophylaxis of diseases is desired, the agent is generally administered orally in the form of a food. When treatment of diseases or recovery of health is desired, the agent is generally administered orally in the form of a pharmaceutical product or food, or administered as an injection, external preparation and the like.

When a serotonin derivative is ingested orally, the daily amount of ingestion of p-coumaroyl serotonin (CS) and feruloyl serotonin (FS) in total is recommended to be 20 to 180 mg, preferably 50 to 150 mg, more preferably 80 to 120 mg. Generally, ingestion or administration in one to several portions a day is preferable. A recommended one ingestion dose is 10 to 180 mg, preferably 25 to 150 mg, more preferably 40 to 120 mg. When one ingestion dose is 1 unit packaging, 5 to 180 mg per 1 unit packaging is recommended, which is preferably 10 to 150 mg, more preferably 20 to 120 mg. Further, when the dosage form is a tablet, capsule, stick-pouch and the like and 1 to 10 thereof can be ingested at one time, the amount per one dosage form or 1 unit packaging is recommended to be 2.5 to 180 mg, preferably 5 to 150 mg, more preferably 10 to 120 mg.

When, for example, an organic solvent extract of a safflower seed is ingested, the daily ingestion is recommended to be 200 to 1500 mg, which is preferably 450 to 1250 mg, more preferably 700 to 1000 mg. Generally, ingestion or administration in one to several portions a day is preferable. A recommended one ingestion dose is 100 to 1500 mg, preferably 250 to 1250 mg, more preferably 400 to 1000 mg. When one ingestion dose is 1 unit packaging, 50 to 1500 mg per 1 unit packaging is recommended, which is preferably 100 to 1250 mg, more preferably 200 to 1000 mg. Further, when the dosage form is tablet, capsule, stick-pouch and the like and 1 to 10 thereof can be ingested at one time, the amount per one dosage form or 1 unit packaging is recommended to be 25 to 1500 mg, preferably 50 to 1250 mg, more preferably 100 to 1000 mg.

The serotonin derivative is contained in various plant seeds, plant tuber and the like, and particularly contained in a large amount in a safflower seed. In Korea, since a safflower seed has been used for promoted cure of bone fracture, prevention of osteoporosis and the like among the people since ancient times, its safety is considered to be high. The results of Example 4 described below have also established that the composition of the present invention is low-toxic and hardly causes adverse effects.

The effects obtained by the agent for improving hemodynamics of the present invention include, for example, improvement of vascular age determined from a second derivative of photoplethysmogram aging index, or a PWV standard value for each chronological age group, prophylaxis of cardiac disease (ventricular hypertrophy, myocardial infarction, angina pectoris, cardiac failure and the like), improvement of hypertension, mitigation of muscle stiffness such as neck stiffness and the like associated with insufficient blood circulation, improvement of sensitivity to cold and the like.

Other features of the invention will become apparent in the course of the following descriptions of exemplary embodiments which are given for illustration of the invention and are not intended to be limiting thereof.

EXAMPLES

Example 1

Preparation of Safflower Seed Extract Containing Serotonin Derivative

A safflower seed extract was prepared by the method described below. Defatted safflower seeds (100 kg) were washed with stirring in 2 kL of water at 30° C. for 30 minutes and then subjected to solid-liquid separation. To the obtained solid content was added 1.5 kL of 60 vol % ethyl alcohol-water. The mixture was heated to 60° C. and stirred at the same temperature for 60 minutes for extraction. Extracts after solid-liquid separation, which were obtained by simultaneously performing the same operation in triplicate, were combined and compression filtered using a filtration aid (KC floc). An aqueous solution of γ-cyclodextrin (CAVAMAX W8 FOOD, manufactured by CycloChem Co. Ltd.) was added in an amount equivalent to that of the solid content of the filtrate, and the mixture was concentrated under reduced pressure at 50 to 60° C. The obtained concentrated solution was heat-sterilized at 88° C. for 1 hour, dried at 60° C. for 15 hours, pulverized and sieved (60 mesh sieve), whereby 6 kg of a safflower seed extract powder was obtained. The analysis results of general components are as shown in Table 1.

TABLE 1

| component | content in 100 g of extract |
|---|---|
| water | 2.1 g |
| protein | 9.8 g |
| lipid | 3.4 g |
| ash | 3.7 g |
| carbohydrates | 80.2 g |
| dietary fiber | 0.8 g |
| energy | 392 kcal |

The total polyphenol content of the safflower seed extract was measured by a Folin-Ciocalteau method and found to be 143 mg/g extract (p-coumaroyl serotonin equivalent amount). HPLC analysis revealed the total serotonin derivative content of 138 mg/g extract (13.8% (w/w)). The results are shown in Table 2. From the results, a serotonin derivative is considered a major component of phenols contained in the safflower seed extract.

TABLE 2

| component | content (mg/g extract) |
|---|---|
| p-coumaroyl serotonin (CS) | 32.2 |
| Feruloyl serotonin (FS) | 31.7 |
| CS monoglucoside | 48.5 |
| FS monoglucoside | 25.7 |
| Total of serotonin derivative | 138.1 |

Example 2

Synthesis of Serotonin Derivative p-Coumaroyl serotonin (CS) and feruloyl serotonin (FS) were synthesized by the following method.

CS: serotonin hydrochloride was dissolved in dimethylformamide (5 mL/g vs. serotonin hydrochloride, hereinafter the same) and dichloromethane (20 mL/g), 1.1 equivalents each of trans-4-coumaric acid (1.0 mol/mol), 1-1-hydroxybenzotriazole hydrate (HOBt), 1-[3-(dimethylamino)propyl]-ethyl-carbodiimide hydrochloride (EDC), and triethylamine were added, and the mixture was reacted with stirring at room temperature overnight. The reaction mixture was concentrated under reduced pressure, ethyl acetate and water (each 40 mL/g serotonin) were added, and the mixture was extracted with ethyl acetate. The extraction phase obtained by 3 times of ethyl acetate extraction was washed successively with 5% aqueous citric acid solution, saturated aqueous sodium hydrogencarbonate solution, and saturated brine, and dried over anhydrous sodium sulfate. The desiccant was removed, and the resulting extract was concentrated under reduced pressure. The residue was crystallized from ethyl acetate-ethanol (10:0.6) and the obtained crystals were washed with ethyl acetate and dried to give CS (yield=69.8%).

FS: Synthesized from serotonin hydrochloride and trans-4-ferulic acid in the same manner as above for CS except that the crystallization was performed using methanol-chloroform (1:15) (yield=69.2%).

Example 3

Blood Pressure and Pulse Wave Improving Effect on Cholesterol Loaded KHC Rabbit

Three-month-old male Kurosawa and Kusanagi-Hypercholesterolemic (KHC) rabbits (genetic hyperlipidemia and atherosclerosis model) were each restrictively fed with 100 g a day of a 0.5% cholesterol-containing test feed added with 4% of the safflower seed extract prepared in Example 1 (safflower seed extract ingestion: about 1.3 g/kg). After feeding the rabbits for 4 weeks (each group: n=6) or 8 weeks (each group: n=3), blood samples were collected from the auricular artery, and the hematobiochemical analyses for blood cholesterol and the like were conducted. The pulse wave was measured according to the method of Katsuda et al. (Katsuda, et. al., *Am. J. Hypertens.*, 17: 181, 2004). To be specific, under pentobarbital anesthesia, one of two catheter pressure transducers was inserted from the left common carotid artery into the ascending aorta (AA), and the other was inserted from the left femoral artery into the distal end of the aortic arch. With confirmation that the blood pressure level was almost stabilized after 1 hour or more from the operation, the pressure pulse waves at the thoracic aortic proximal portion (Position 1; P.1), thoracic aortic midportion (Position 2; P.2), thoracic aortic distal portion (Position 3; P.3), abdominal aortic proximal portion (Position 4; P.4), abdominal aortic midportion (Position 5; P.5) and abdominal aortic distal portion (Position 6; P.6) were each recorded simultaneously with an ascending aortic pressure pulse wave for about 60 seconds on a computer via an analog-digital (A/D) converter, by moving the tip of the catheter transducer inserted from the common iliac artery by 80 mm at a time from the distal end of the aortic arch (Position 0; P.0) to the vicinity of the common iliac artery branch. Of the pressure pulse waves thus recorded, the second derivative of photoplethysmogram of the original waveform in a continuous 50-heartbeat cycle was calculated on a computer based on a stable 30-second record of each part, and the time point of the peak was taken as the rise point of the pressure pulse wave. Local pulse wave velocity (LPWV) was calculated as $\Delta D/\Delta T$ based on the time-lag ($\Delta T$) in the pressure pulse wave rise points recorded at two adjacent points and the distance ($\Delta D$) between the two adjacent points. As the distance between AA and P.0 or P.1, the distance ($\Delta D$ total) between the left femoral artery catheter insertion part and the catheter transducer pressure sensor placed in the ascending aorta was precisely measured in situ. The distance between AA-P.0 was $\Delta D$ total-320 mm, and the distance between AA-P.1 was $\Delta D$ total-280 mm. The pulse wave velocity (aortic PWV) in the entire aorta was calculated as the velocity from AA to P.6.

Augmentation Index (AIx) was calculated according to the following method. The fourth derivative of photoplethysmogram was calculated from the original waveform of a pressure pulse wave recorded in the computer, and the time point when this crosses with the baseline for the second time from the upward to the downward within one heartbeat cycle was taken as the peak (P1) of the systolic anterior component, and the amplitude of the systolic posterior component, i.e., pulse pressure, was taken as P2. AIx was calculated as P2/P1 and further calculated as (P2-P1)/P2×100(%).

After the completion of blood pressure measurement, the rabbits were euthanized, and the aorta from the root to the common iliac artery branch was removed. It was cut in the longitudinal direction, and the plaque area of the exposed intimal surface was measured using an image analyzer.

Hematobiochemistry: During the 4 weeks of administration tests, no difference in the total blood cholesterol from the control group (0.5% cholesterol feed) was observed. Moreover, other lipids (HDL-cholesterol, triglyceride, phospholipid, lipoperoxide (LPO)), blood glucose, hepatic function indices (GOT, GPT, total protein, albumin), renal function indices (urea nitrogen, creatinine), electrolytes ($Na^+$, $K^+$, $Ca^{2+}$, $Mg^{2+}$, $Cl^-$), and blood pressure-related hormones (rennin-angiotensin-aldosterones, rennin-angiotensin-converting enzyme activity, angiotensin I, angiotensin II) did not show a great change due to the administration of the safflower seed extract.

Figure 2:
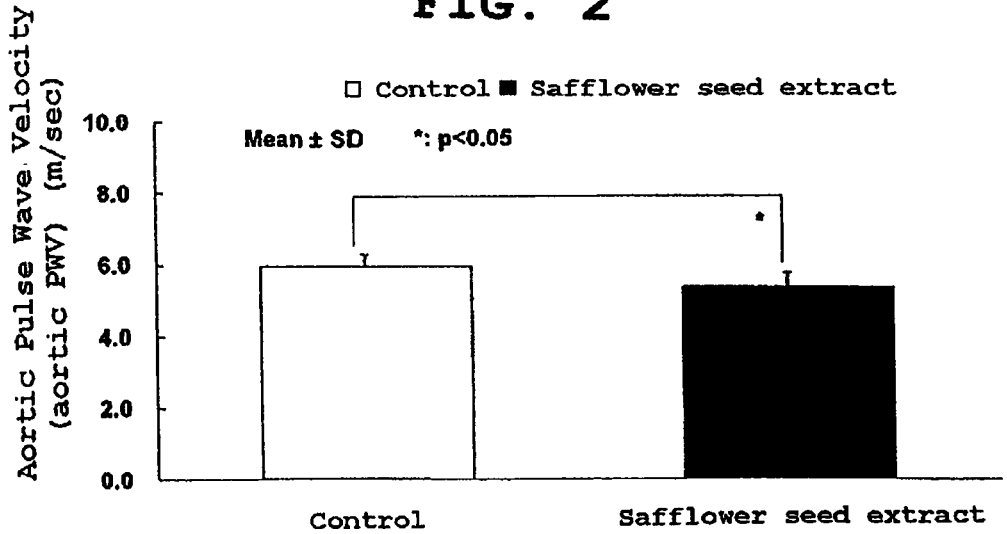
FIG. 2 shows pulse wave velocity (aortic PWV) in the whole of 4 week cholesterol loaded KHC rabbit aorta in Example 3.
Figure 3:
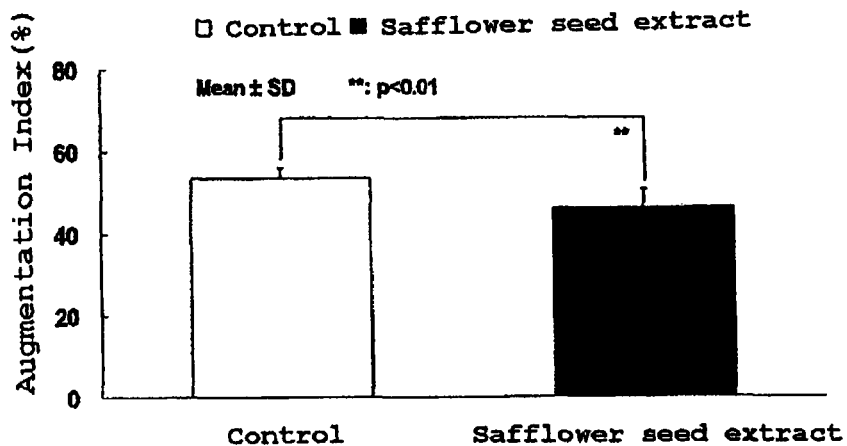
FIG. 3 shows Augmentation index (AIX) in 4 week cholesterol loaded KHC rabbit in Example 3.
Figure 4:
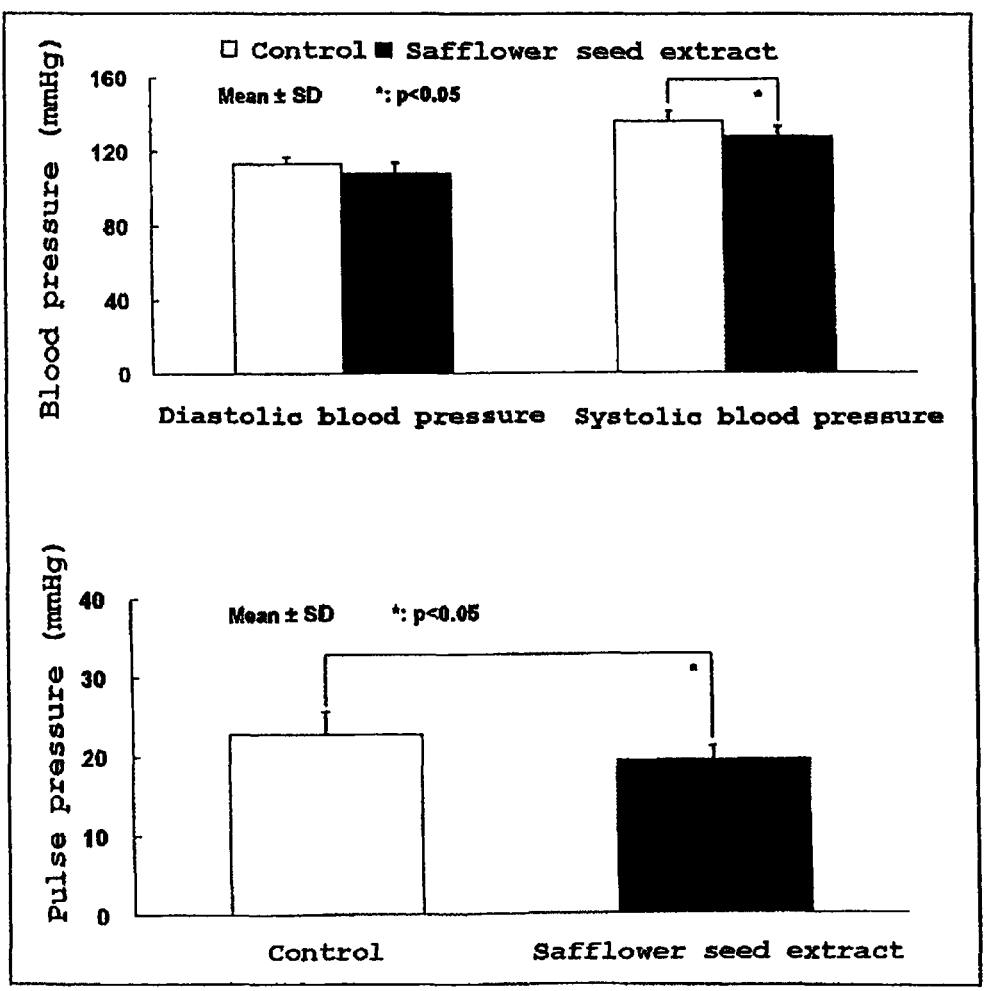
FIG. 4 shows the diastolic and systolic blood pressures in the upper Figure, and the pulse pressure (systolic blood pressure-diastolic blood pressure) in the lower Figure, respectively, in 4 week cholesterol loaded KHC rabbit in Example 3.

Action on blood pressure and pulse wave: By comparison of the local pulse wave velocities (LPWVs) in the aorta, the safflower seed extract administration group showed a significant decrease in P.1-P.2 and P.4-P.5 (see, FIG. 1) as compared to the control group (see, FIG. 1). Moreover, the pulse wave velocity in the entire aorta (aortic PWV) from the root (AA) to the common iliac artery branch (P.6) showed a significant decrease in the administration group (see, FIG. 2). A significant decrease in AIx was also observed as compared to the control group (see, FIG. 3). While the diastolic blood pressure showed a tendency toward a slight decrease in the administration group, the difference was not significant. On the other hand, the systolic blood pressure and pulse pressure decreased significantly in the administration group (see, FIG. 4).

Action on atherosclerosis lesion formation: Lesion area was calculated for each of the regions divided at pulse wave measurement points AA, P.0, P.1, P.2, P.3, P.4, P.5 and P.6. In the respective regions, the lesion area significantly decreased in the administration group in AA-P.0, but either a decreasing tendency or no change was observed in other regions except P.4-P.5. In P.1-P.2 and P.4-P.5 where LPWV significantly decreased, the lesion area did not decrease. While the lesion area in the whole aorta in the administration group showed a decreasing tendency, a significant difference was not found.

Although no statistically significant difference was obtained due to the small number of each group in the 8 week administration test, both PWV and AIx showed similar results as in the 4 week administration test.

These results have clarified that a safflower seed extract containing a serotonin derivative as a primary phenol component does not greatly affect blood lipid and other hematobiochemistry, and improves hemodynamics indices such as pulse wave velocity (LPWV, aortic PWV), AIx, blood pressure and the like. No correlation was observed between the LPWV and the atherosclerosis lesion area and structural stiffness such as fibril formation, calcification and the like is unlikely to be developed in a relatively young animal within the short period of 4 weeks of cholesterol loading (Katsuda, et. al., *Physiol. Meas.*, 25: 505, 2004). Therefore, safflower seed extract was considered to have improved the hemodynamics by mainly decreasing the total vascular resistance by improving the vascular function.

Example 4

Safety Test of Safflower Seed Extract

The safflower seed extract prepared in Example 1 was applied to a toxicity test by 4 week repetitive oral administration to rats.

Test animal: Crj:CD(SD)IGS male and female rats (age at start of administration=6-week-old, 6 rats/group)

Administration: The safflower seed extract prepared in Example 1 was added to a feed at concentrations of 0, 2.5, 5, and 10% (w/w), and the rats were allowed to freely eat the feed. For confirmation of an influence of γ-cyclodextrin (γCD) contained as an excipient, an excipient control group with the addition of γCD at a concentration of 5% (w/w) was established.

Observation, test, and measurement: observation of general condition, body weight measurement, measurement of food consumption, urine test, hematological test, hematobiochemical test, biopsy, organ weight measurement and histopathological test were performed.

The results are shown in Table 3.

TABLE 3

| concentration (% (w/w)) in feed | | 0 | 2.5 | 5.0 | 10.0 | γCD (5.0) |
|---|---|---|---|---|---|---|
| dose (mg/kg/day) | ♂ | 0 | 1888 | 3684 | 7768 | 3736 |
|  | ♀ | 0 | 1995 | 4020 | 7955 | 4048 |
| animal number (♂/♀) |  | 6/6 | 6/6 | 6/6 | 6/6 | 6/6 |
| number of deaths (♂/♀) |  | 0/0 | 0/0 | 0/0 | 0/0 | 0/0 |
| body weight gain (g) (day 0-28) | ♂ | 187.0 ± 17.55 | 177.2 ± 18.99 | 183.0 ± 12.52 | 172.5 ± 18.81 | 196.8 ± 11.14 |
|  | ♀ | 70.0 ± 7.43 | 69.8 ± 6.91 | 60.2 ± 15.51 | 53.3 ± 16.11 | 78.3 ± 7.92 |
| ingestion amount (g) (day 0-28) | ♂ | 654.7 | 668.4 | 636.3 | 670.8 | 683.1 |
|  | ♀ | 469.2 | 454.3 | 449.1 | 432.8 | 478.1 |
| GLU (mg/dL) | ♂ | 122 ± 12 | 134 ± 17 | 135 ± 8 | 127 ± 7 | 131 ± 23 |
|  | ♀ | 114 ± 11 | 125 ± 18 | 111 ± 12 | 113 ± 20 | 130 ± 9 |
| TG (mg/dL) | ♂ | 33.7 ± 25.3 | 31.6 ± 14.3 | 23.1 ± 11.0 | 23.1 ± 11.2 | 35.7 ± 24.4 |
|  | ♀ | 6.9 ± 7.1 | 7.9 ± 3.6 | 5.3 ± 2.1 | 5.3 ± 1.9 | 8.6 ± 5.9 |
| Na (mEq/L) | ♂ | 145.3 ± 1.1 | 145.3 ± 0.9 | 145.5 ± 0.6 | 145.2 ± 0.9 | 144.9 ± 1.0 |
|  | ♀ | 143.8 ± 0.7 | 144.7 ± 0.9 | 145.1 ± 1.1 | 145.3 ± 1.1 | 144.1 ± 1.0 |
| liver weight (g) | ♂ | 10.48 ± 1.12 | 11.16 ± 1.20 | 11.22 ± 1.01 | 10.62 ± 0.85 | 11.48 ± 1.09 |
|  | ♀ | 6.13 ± 0.53 | 6.64 ± 0.43 | 6.45 ± 0.45 | 6.51 ± 0.52 | 6.81 ± 0.68 |
| anatomy |  | — | — | — | — | — |

Appreciable observation: none
*: $p < 0.05$

The dose in this test based on the food intake was as high as about 2 g/kg/day (2.5% group) to about 8 g/kg/day (10% group). However, no death occurred in all the administration groups. As a result of the hematobiochemical test, tissue test and organ weight, no significant toxicological change was observed. Therefore, it has been demonstrated that the agent for improving hemodynamics of the present invention is sufficiently safe.

Example 5

Pulse Wave Improvement Effect in Human

Preparation of Test Diet.

The safflower seed extract prepared in Example 1 was filled in a hard capsule by a hard capsule filling machine (Ultra 8, manufactured by Capsugel Japan Inc.) (210 mg of safflower seed extract per one capsule, containing about 29 mg of serotonin derivative). Evaluation of pulse wave improvement effect.

90 male volunteers underwent tests for a second derivative of photoplethysmogram and a brachial-ankle pulse wave velocity (baPWV) in advance, and 20 therefrom who had a high vascular age and free of a drug treatment for blood pressure, blood cholesterol or blood glucose were selected as test subjects (age: 30 to 55 years old (37.3±6.8 years old)). A test diet (safflower seed extract 2.1 g (about 290 mg as serotonin derivative)) was given two times a day (morning and evening, within 30 minutes after meal) for 4 weeks, and the blood pressure and baPWV were measured, and blood samples were collected immediately before intake and after 4-week intake of test food. Subjects were advised not to take pharmaceutical agents and supplements influential on the blood pressure, lipid and the like during the test period. For measurement of the blood pressure and baPWV, a blood pressure pulse wave test apparatus (form PWV/ABI, Colin Medical Technology Corporation) was used. The systolic blood pressure of the volunteers before test diet intake was 125.9±14.0 mmHg for the left brachial and 128.8±14.5 mmHg for the right brachial, and baPWV was 1318.6±120.5 cm/s for the left brachial-left ankle and 1317.9±124.3 cm/s for the right brachial-right ankle (average value±standard deviation), respectively. Blood samples were collected from the cubital median vein in the sitting and resting state, and subjected to general biochemical analyses such as blood cholesterol and the like. Breakfast was not allowed before and after intake on the day of the test, and the collection of blood and the measurements were performed during fasting.

During the test diet intake period, no symptom considered to have been caused by the test diet was reported. Blood biochemical parameters (blood lipid (total cholesterol, HDL-cholesterol, LDL-cholesterol, triglyceride), and blood glucose, liver function indices (GOT, GPT, LDH, γ-GTP total protein, albumin), renal function indices (urea nitrogen, creatinine) and electrolytes ($Na^+$, $K^+$, $Ca^{2+}$)) did not show an abnormal change before and after the intake.

Figure 5:
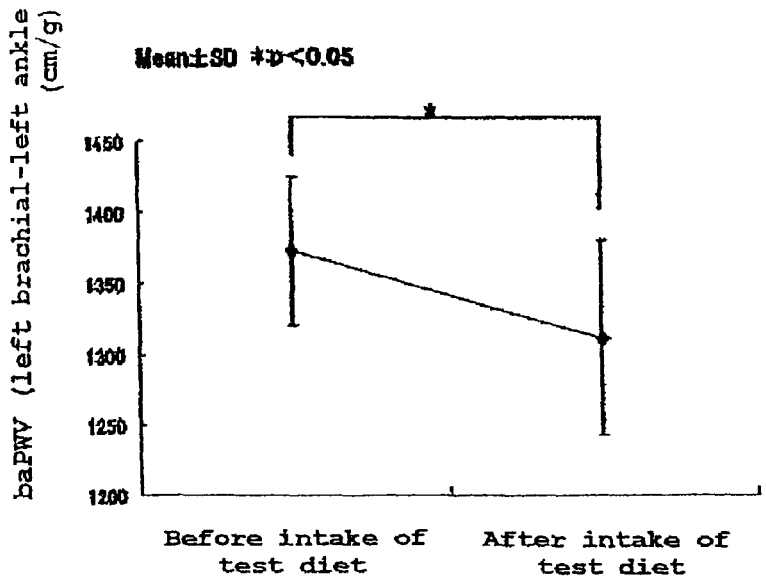
FIG. 5 shows changes in baPWV in left brachial-left ankle between before and after intake of a test diet by a volunteer who showed a systolic blood pressure of not less than 130 mmHg on average by a preliminary test, and the test value immediately before start of the ingestion of the test food in Example 5.

Moreover, 6 test subjects (142.5±13.4 mmHg) who showed the average systolic blood pressure of the right brachial and left brachial of not less than 130 mmHg on average of the preliminary test values and the test values of immediately before start of the test diet intake were analyzed. As a result, baPWV from left brachial-left ankle showed a significant decrease from 1373.0±52.5 cm/s (before test diet intake) to (1311.8±69.2 cm/s) after test diet intake (see, FIG. 5).

From these results, it is considered that a safflower seed extract can be taken safely, and decreases baPWV, i.e., improves vascular age, particularly in human showing a tendency toward high blood pressure.

Example 6

Blood Pressure and Pulse Wave Improving Effect in Cholesterol Loaded KHC Rabbit

Two to three-month-old male Kurosawa and Kusanagi-Hypercholesterolemic (KHC) rabbits (genetic hyperlipidemia and atherosclerosis model) were each restrictively fed with 100 g a day of a 0.5% cholesterol-containing test feed added with 4% of the safflower seed extract prepared in Example 1 or 0.55% of the serotonin derivative synthesized by the method of Example 2 (p-coumaroyl serotonin (CS) 0.32%, feruloyl serotonin (FS) 0.23%) (control group n=5, safflower seed extract administration group n=5, serotonin derivative administration group n=6). After feeding for 8 weeks, blood samples were collected from the auricular artery, and the hematobiochemical analyses for blood cholesterol and the like were conducted. In the same manner as in Example 3, pulse wave velocity, AIx and blood pressure were measured and the lesion area was analyzed. The 8 week feeding test data of Example 3 were added for the analyses of all of AIx, pulse wave velocity other than blood pressure, lesion area, hematobiochemical index and the like.

Hematobiochemistry: During the 8 weeks of administration tests, no difference in the total blood cholesterol from the control group (0.5% cholesterol feed) was observed. Moreover, other lipids (HDL-cholesterol, triglyceride, phospholipid, lipoperoxide (LPO)), blood glucose, hepatic function indices (GOT, GPT, total protein, albumin), renal function indices (urea nitrogen, creatinine), electrolytes ($Na^+$, $K^+$, $Ca^{2+}$, $Mg^{2+}$, $Cl^-$), and blood pressure-related hormones (rennin-angiotensin-aldosterones, rennin-angiotensin-converting enzyme activity, angiotensin I, angiotensin II) did not show a great change due to the administration of the safflower seed extract and serotonin derivative.

Figure 6:
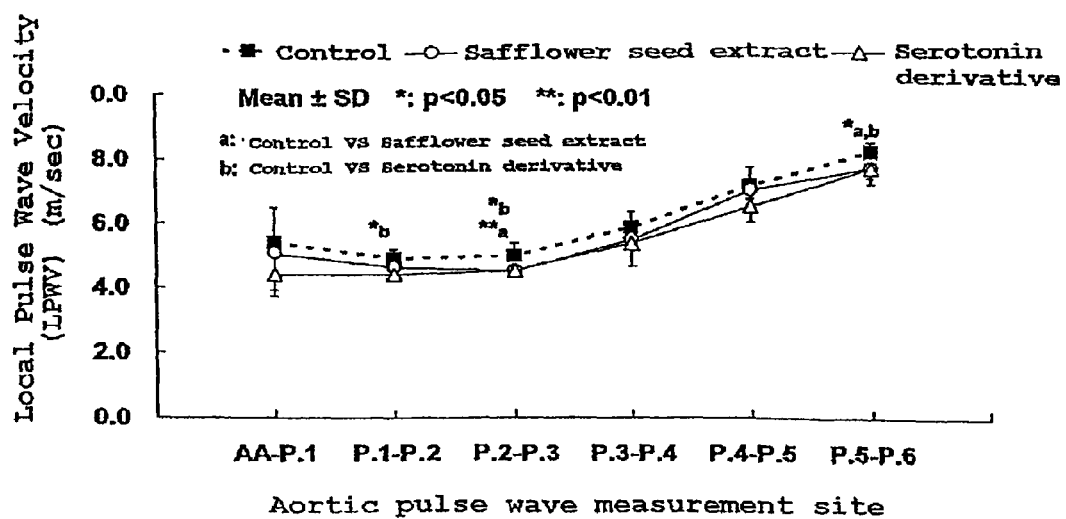
FIG. 6 shows local pulse wave velocity (LPWV) in 8 week cholesterol loaded KHC rabbit aorta in Example 6. The horizontal axis shows an aortic region where the pressure pulse wave was measured (AA-P.0=ascending aorta-distal end of aortic arch, P.0-P.1=distal end of aortic arch-thoracic aortic proximal portion, P.1-P.2=thoracic aortic proximal portion-thoracic aortic midportion, P.2-P.3=thoracic aortic midportion-thoracic aortic distal portion, P.3-P.4=thoracic aortic distal portion-abdominal aortic proximal portion, P.4-P.S=abdominal aortic proximal portion-abdominal aortic midportion, P.5-P.6=abdominal aortic midportion-abdominal aortic distal portion).
Figure 7:
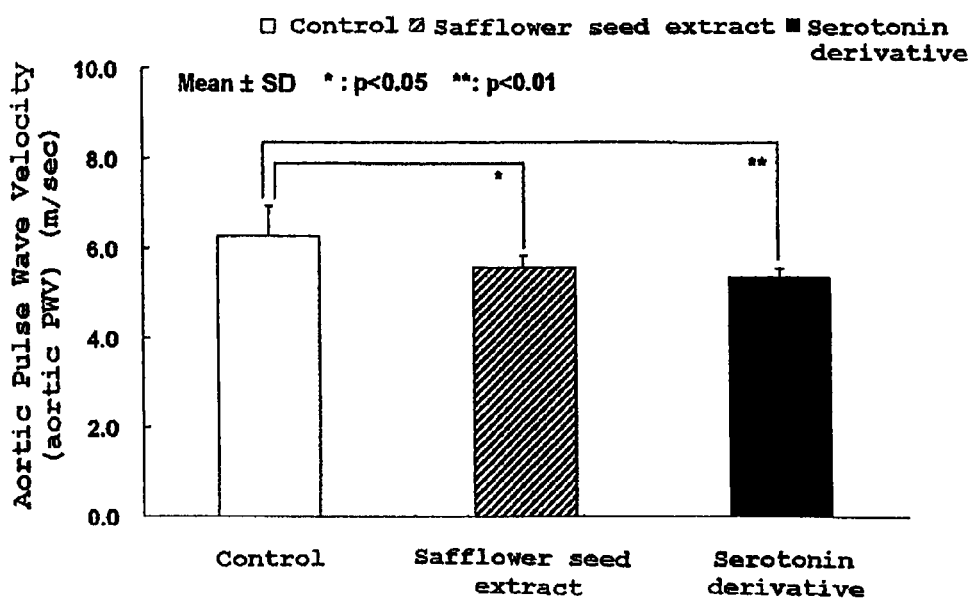
FIG. 7 shows pulse wave velocity (aortic PWV) in the whole 8 week cholesterol loaded KHC rabbit aorta in Example 6.
Figure 8:
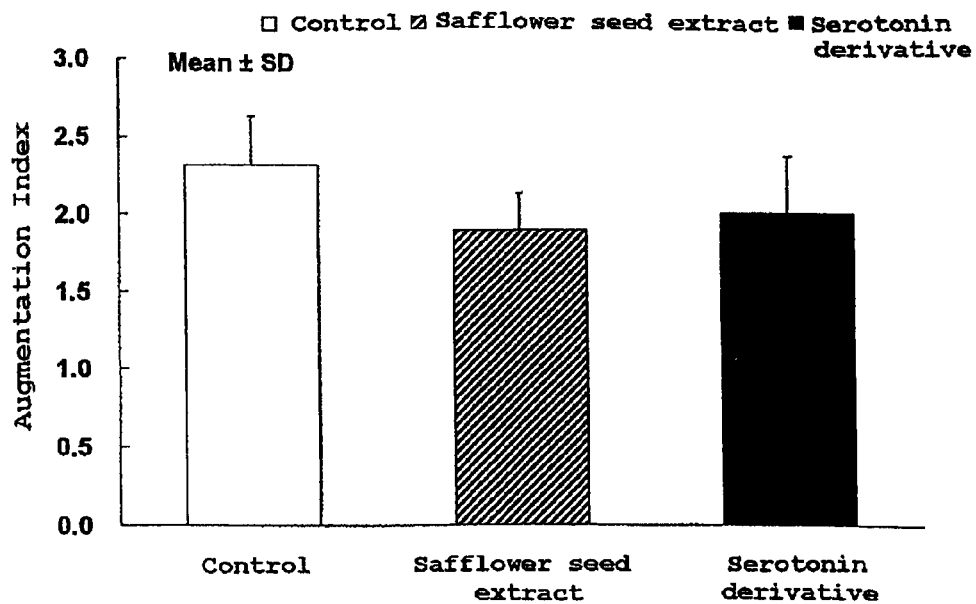
FIG. 8 shows Augmentation index (AIx) in 8 week cholesterol loaded KHC rabbit in Example 6.

Action on blood pressure and pulse wave: By comparison of the local pulse wave velocities (LPWVs) in the aorta, the safflower seed extract administration group showed a significant decrease in P.2-P.3 and P.5-P.6 and the serotonin derivative administration group showed a significant decrease in P.1-P.2, P.2-P.3 and P.5-P.6 (see, FIG. 6), as compared to the control group. Moreover, the pulse wave velocity in the entire aorta (aortic PWV) from the ascending aorta (AA) to the abdominal aortic distal portion (P.6) showed a significant decrease in each administration group (see, FIG. 7). While AIx was not statistically significant as compared to the control group, each administration group showed a decreasing tendency (see, FIG. 8). In addition, the systolic blood pressure and diastolic blood pressure also showed a decreasing tendency in each administration group.

Figure 9:
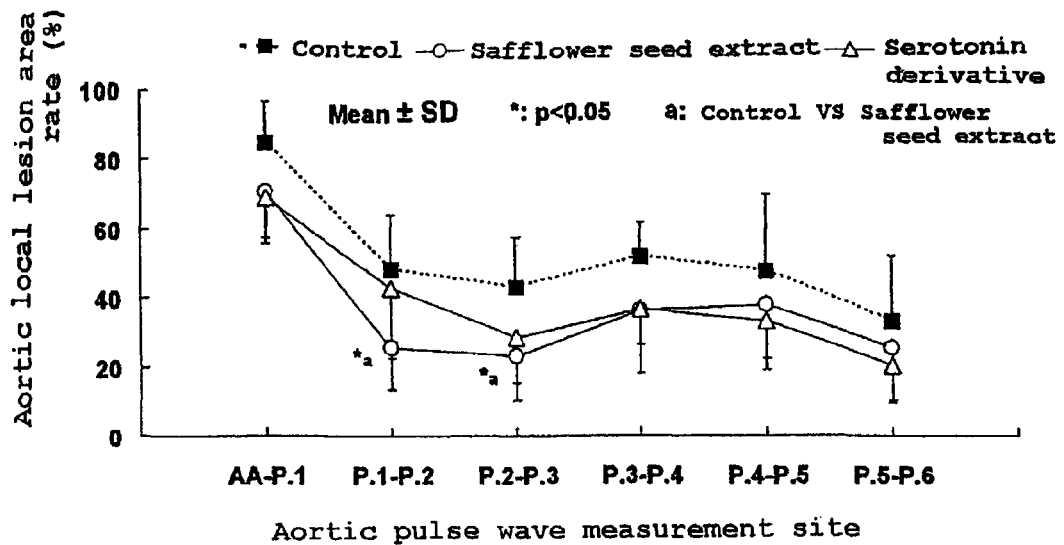
FIG. 9 shows an aortic local lesion in 8 week cholesterol loaded KHC rabbit in Example 6. The horizontal axis shows an aortic region where the pressure pulse wave was measured (AA-P.0=ascending aorta-distal end of aortic arch, P.0-P.1=distal end of aortic arch-thoracic aortic proximal portion, P.1-P.2=thoracic aortic proximal portion-thoracic aortic midportion, P.2-P.3=thoracic aortic midportion-thoracic aortic distal portion, P.3-P.4=thoracic aortic distal portion-abdominal aortic proximal portion, P.4-P.5=abdominal aortic proximal portion-abdominal aortic midportion, P.5-P.6=abdominal aortic midportion-abdominal aortic distal portion).
Figure 10:
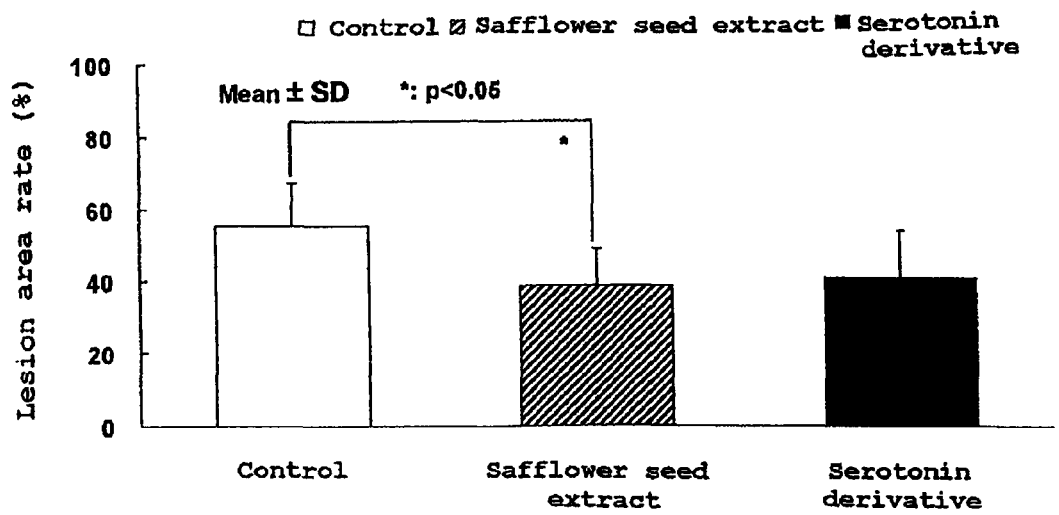
FIG. 10 shows a total aortic lesion area in 8 week cholesterol loaded KHC rabbit in Example 6.

Action on atherosclerosis lesion formation: Lesion area was calculated for each of the regions divided at pulse wave measurement points AA, P.1, P.2, P.3, P.4, P.5 and P.6. The lesion areas in P.1-P.2 and P.2-P.3 significantly decreased in the safflower seed extract administration group. In other areas, the safflower seed extract administration group and serotonin derivative administration group showed a decreasing tendency, although significant difference was not observed (see, FIG. 9). On the other hand, the safflower seed extract administration group showed a significant difference in the entire aorta lesion area. The serotonin derivative administration group showed a decreasing tendency, although significant difference was not observed (see, FIG. 10).

Figure 11:
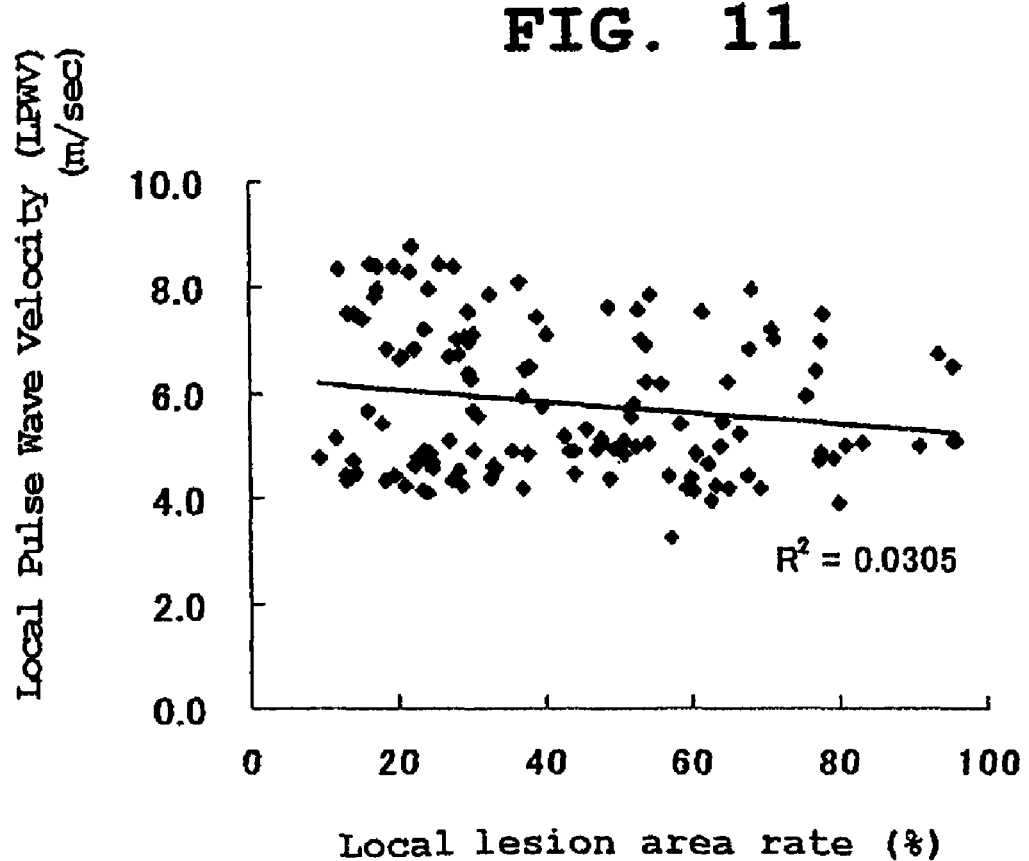
FIG. 11 shows the relationship between the local pulse wave velocity (LPWV) and the lesion area in the same position in Example 6.

These results have clarified that a serotonin derivative and a safflower seed extract containing the same as a primary phenol component does not greatly affect blood lipid and other hematobiochemistry, and improves hemodynamics indices such as pulse wave velocity (LPWV, aortic PWV), AIx, blood pressure and the like. Since no correlation was observed between the LPWV and the atherosclerosis lesion area as shown in FIG. 11 and structural stiffness such as fibril formation, calcification and the like is unlikely to be developed in a relatively young animal within the short period of 8 weeks of cholesterol loading (Katsuda, et. al., *Physiol. Meas.*, 25: 505, 2004), the serotonin derivative and safflower seed extract was considered to have improved the hemodynamics by mainly decreasing the total vascular resistance by improving the vascular function.

INDUSTRIAL APPLICABILITY

The agent for improving hemodynamics provided by the present invention effectively prevents or improves deterioration of hemodynamics associated with aging and cardiovascular diseases, and is useful for the maintenance and enhancement for health. The agent is highly safe, can be used as a pharmaceutical agent, is useful as a food, and is industrially extremely useful.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A method of improving hemodynamics, comprising orally administering to a subject in need thereof an effective amount of at least one serotonin derivative selected from the group of compounds represented by formula (I):

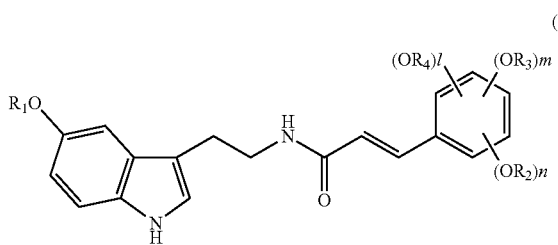

wherein $R_1$, $R_2$, $R_3$, and $R_4$ are each independently a hydrogen atom, or an alkyl group having 1 to 3 carbon atoms, and n, m, and l are each 0 or 1, or a glycoside thereof.

2. The method of claim 1, wherein said improving hemodynamics effects at least one improvement selected from the group consisting of improvement of vascular age, improvement of blood pressure, and improvement of pulse pressure.

3. The method of claim 2, wherein said improvement of vascular age is at least one improvement selected from the group consisting of improvement of a pulse wave velocity (PWV), improvement of Augmentation Index (AIx), improvement of second derivative of photoplethysmogram waveform and improvement of a second derivative of photoplethysmogram aging index.

4. The method of claim 1, wherein said at least one compound is at least one member selected from the group consisting of serotoninamide of hydroxycinnamic acid and a glycoside thereof.

5. The method of claim 4, wherein said hydroxycinnamic acid is at least one member selected from the group consisting of p-coumaric acid, ferulic acid and caffeic acid.

6. The method of claim 1, wherein said at least one serotonin derivative is contained in an extract from a plant tissue.

7. The method of claim 6, wherein said plant tissue is a safflower seed.

8. The method of claim 1, wherein said at least one serotonin derivative is contained in an organic solvent extract from a safflower seed before or after oil extraction.

9. The method of claim 1, which comprises administering either p-coumaroyl serotonin or feruloyl serotonin.

10. The method of claim 9, wherein said at least one serotonin derivative is administered in a total daily amount of 20 to 180 mg.

11. The method of claim 9, wherein said at least one serotonin derivative is administered in a total daily amount of 50 to 150 mg.

12. The method of claim 8, wherein said at least one serotonin derivative is administered in a total daily amount of 200 to 1500 mg.

13. The method of claim 8, wherein said at least one serotonin derivative is administered in a total daily amount of 450 to 1250 mg.

14. A method according to claim 1, which is a method of improving blood pressure.

15. A method according to claim 1, which is a method of improving pulse pressure.

16. A method according to claim 1, which is a method of improving pulse wave velocity.

17. A method according to claim 1, which is a method of improving Augmentation Index.

18. A method according to claim 1, which is a method of improving second derivative of photoplethysmogram wave form.

19. A method according to claim 1, which is a method of improving second derivative of photoplethysmogram aging index.